(12) United States Patent
Sakai et al.

(10) Patent No.: US 9,918,951 B2
(45) Date of Patent: Mar. 20, 2018

(54) METHOD FOR IMPROVING STORAGE STABILITY OF GLUTATHIONE

(75) Inventors: Yasushi Sakai, Tsukuba (JP); Shun Kayahashi, Tsukuba (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 12/866,001

(22) PCT Filed: Feb. 5, 2009

(86) PCT No.: PCT/JP2009/051944
§ 371 (c)(1),
(2), (4) Date: Aug. 3, 2010

(87) PCT Pub. No.: WO2009/099132
PCT Pub. Date: Aug. 13, 2009

(65) Prior Publication Data
US 2010/0311837 A1    Dec. 9, 2010

(30) Foreign Application Priority Data
Feb. 5, 2008  (JP) ................................. 2008-024855

(51) Int. Cl.
*A61K 9/00* (2006.01)
*A61K 31/198* (2006.01)
*A61K 9/14* (2006.01)
*A61K 47/12* (2006.01)
*A61K 47/18* (2017.01)
*A23L 33/10* (2016.01)
*A23L 33/175* (2016.01)

(52) U.S. Cl.
CPC ............ *A61K 31/198* (2013.01); *A23L 33/10* (2016.08); *A23L 33/175* (2016.08); *A61K 9/145* (2013.01); *A61K 47/12* (2013.01); *A61K 47/183* (2013.01); *A23V 2002/00* (2013.01)

(58) Field of Classification Search
USPC .......................................................... 424/400
See application file for complete search history.

(56) References Cited

U.S. PATENT DOCUMENTS 2,665,901 A * 1/1954 Patterson ..................... 267/125
2,665,991 A * 1/1954 Kuhrt ............................ 426/544
2,935,449 A * 5/1960 Bavley et al. ................ 514/529
6,204,248 B1   3/2001 Demopoulos et al.
6,274,553 B1   8/2001 Furuya et al.
2005/0019399 A1 * 1/2005 Fischer et al. .............. 424/468

FOREIGN PATENT DOCUMENTS

| CA | 2276183 C | 6/2009 |
|---|---|---|
| JP | 47-025312 A | 10/1972 |
| JP | 64-063342 A | 3/1989 |
| JP | 03-052821 A | 3/1991 |
| JP | 05-176739 A | 7/1993 |
| JP | 10-259138 A | 9/1998 |
| JP | 2001-507696 A | 6/2001 |
| JP | 2001-190245 A | 7/2001 |
| JP | 2002-097153 A | 4/2002 |
| WO | WO 1992/021368 A1 | 12/1992 |
| WO | WO 2008/041740 A1 | 4/2008 |

OTHER PUBLICATIONS

Machine translation of JP 2001-507696.*
Brunini et al. (Cardiovascular Research 73 (2007) 359-367).*
Das et al. (Molecular and Cellular Biochemistry 285: 143-147, 2006).*
Passion Rx (http://www.passionrx.net/largininebenefit.html; Oct. 15, 2007).*
Preli (Atherosclerosis 162 (2002) 1-15).*
Hanson (http://www.angelhealingcenter.com/AmalgamProtocol.html, excerpted from Hanson, Dental Mercury Detox (Health Information Guide Series), Bio-Probe, Inc., 1997).*
Sugino (J. Clin. Biochem. Nutr., 41, 224-230, Nov. 2007).*
Amazon (http://www.amazon.com/Dental-Mercury-Detox-HealthInformation/dp/0941011054/ref=sr_1_fkmr0_1?ie=UTF8&qid=1421373851&sr=8-1-fkmr0&keywords=hansen+dental+mercury+detox, accessed Jan. 15, 2015).*

* cited by examiner

*Primary Examiner* — Devang K Thakor
(74) *Attorney, Agent, or Firm* — Leydig, Voit & Mayer, Ltd.

(57) ABSTRACT

The invention provides a method of improving the preservation stability of glutathione in a solid composition containing glutathione and arginine. In particular, glutathione and arginine are made to be coexistent with an organic acid such as citric acid, tartaric acid, ascorbic acid, malic acid, malonic acid, succinic acid, fumaric acid, maleic acid and the like. The amount of the organic acid to coexistent with glutathione and arginine is generally 0.1-2 parts by weight relative to 1 part by weight of arginine.

9 Claims, No Drawings

METHOD FOR IMPROVING STORAGE STABILITY OF GLUTATHIONE

TECHNICAL FIELD

The present invention relates to a solid composition containing glutathione and arginine, and a method of improving preservation stability of glutathione in the solid composition.

BACKGROUND ART

Glutathione is an antioxidant substance in the body, and has been reported to show physiological activities of whitening, anti-aging and hyperglycemia suppressive action based on the antioxidant action. In addition, since the content of glutathione decreases in cells such as T lymphocyte and the like in human showing decreased immune function (see non-patent document 1), supply of glutathione from the outside is considered to enhance the immune function.

However, glutathione shows decreased quality by influences of heat, oxygen, light and the like and, as a result, may cause an unpleasant odor like sulfur, a decreased content and the like in a preparation.

As a method of suppressing decrease of the quality of glutathione, a method including coating the surface of the particles of a glutathione powder (see patent documents 1 and 2), a method including adding cyclodextrin (see patent documents 1 and 3) and the like are known. However, these methods are problematic in that the operation is complicated, the effect is weak, and the like.

On the other hand, arginine is known as a synthesis substrate for protein, polyamine, nitric oxide and the like in the body. Reported physiological actions of arginine include an immunostimulating action (see non-patent document 2), a muscle-building action, a nitric oxide production promoting activity, a wound healing activity and the like.

Thus, both glutathione and arginine have various physiological actions including common physiological actions such as immunostimulating action and the like. Hence, simultaneously ingestion of glutathione and arginine is expected to afford not only an additive effect but also a synergistic effect of each of the physiological actions.

However, it has not been known that the coexistence of glutathione and arginine markedly decreases the quality of glutathione.

patent document 1: JP-A-5-176739
patent document 2: JP-A-2002-97153
patent document 3: JP-A-64-63342
non-patent document 1: "Pediatric Infectious Disease Journal" 1998, vol. 17, No. 3, p. 236-241
non-patent document 2: "Surgery", 1990, vol. 108, No. 2, p. 331-337

DISCLOSURE OF THE INVENTION

Problems to be Solved by the Invention

An object of the present invention is to provide a method of improving preservation stability of glutathione in a solid composition containing glutathione and arginine, or a solid composition containing glutathione and arginine, which shows improved preservation stability of glutathione.

Means of Solving the Problems

The present invention relates to the following (1)-(6).
(1) A method of improving preservation stability of glutathione in a solid composition containing glutathione and arginine, which comprises achieving coexistence of glutathione and arginine, with an organic acid.
(2) The method of the above-mentioned (1), wherein the solid composition is a solid preparation.
(3) The method of the above-mentioned (1) or (2), wherein the organic acid is selected from citric acid, tartaric acid, ascorbic acid and malic acid.
(4) The method of any one of the above-mentioned (1)-(3), wherein the organic acid is citric acid or tartaric acid.
(5) A solid composition comprising glutathione, arginine, and citric acid or tartaric acid.
(6) A solid preparation comprising glutathione, arginine, and citric acid or tartaric acid.

Effect of the Invention

The present invention can provide a method of improving preservation stability of glutathione in a solid composition containing glutathione and arginine, or a solid composition containing glutathione and arginine, which shows improved preservation stability of glutathione.

BEST MODE FOR CARRYING OUT THE INVENTION

As a method of improving preservation stability of glutathione in a solid composition containing glutathione and arginine of the present invention (hereinafter to be also referred to as a method of improving preservation stability of glutathione of the present invention), a method including achieving coexistence of glutathione and arginine, with organic acid according to a method such as mixing and the like to give a solid composition can be mentioned.

Glutathione to be used in the present invention may be any of a reduced form (L-γ-glutamyl-L-cysteinylglycine) and an oxidized form (glutathione disulfide).

Glutathione may be any of a powder, a particulate and a mixture thereof, or may be contained in a glutathione-containing product such as a yeast extract and the like. The water content is preferably not more than 5 wt %, more preferably not more than 3 wt %.

Arginine in the present invention may be any of an L form and a D form, with preference given to an L form.

Arginine may be a salt of an inorganic acid such as hydrochloride, sulfate, phosphate and the like, with preference given to a free form.

Arginine may be any of a powder, a particulate and a mixture thereof. The water content is preferably not more than 3 wt %, more preferably not more than 1 wt %, and still more preferably not more than 0.3 wt %.

While the organic acid to be coexistent with glutathione and arginine may be any organic acid as long as it is solid at ambient temperature. From the aspect of use for pharmaceutical products, foods and drinks, feed and the like, lactic acid, tartaric acid, ascorbic acid, malic acid, malonic acid, succinic acid, fumaric acid, maleic acid, citric acid and the like can be mentioned. Citric acid, tartaric acid, ascorbic acid and malic acid are preferable, citric acid, tartaric acid and ascorbic acid are more preferable, and citric acid and tartaric acid are still more preferably used.

The organic acid may be any of a powder, a particulate and a mixture thereof. The water content is preferably not more than 3 wt %, more preferably not more than 1 wt %, and still more preferably not more than 0.3 wt %.

The amount of the organic acid to be coexistent with glutathione and arginine is generally 0.1-2 parts by weight, preferably 0.2-1.2 parts by weight, more preferably 0.4-0.8 part by weight, relative to 1 part by weight of arginine.

The amounts of glutathione and arginine are generally 1-100 parts by weight, preferably 1-50 parts by weight, more preferably 1-20 parts by weight, of arginine relative to 1 part by weight of glutathione.

When glutathione and arginine are coexistent with organic acid, a substance generally used in the field of pharmaceutical product, food or feed, which does not adversely influence the preservation stability of glutathione, may be further added.

Examples of the substance generally used in the field of pharmaceutical product, food or feed include base for preparations such as excipient, disintegrant, binder, lubricant and the like, sweetening agent, colorant, flavor, antioxidant, glidant and the like.

Examples of the excipient include maltose, trehalose, mannitol, hydrogenated maltose starch syrup, lactitol, xylitol, sorbitol, erythritol, crystalline cellulose, low-substituted hydroxypropylcellulose and the like.

Examples of the disintegrant include carboxymethylcellulose, calcium carboxymethylcellulose, sodium carboxymethylcellulose, crospovidone, croscarmellose sodium, sodium glycolate, starch such as cornstarch, potato starch, partly pregelatinized starch and the like, and the like.

Examples of the binder include polyvinylpyrrolidone, pullulan, methylcellulose, hydroxypropylcellulose, polyvinyl alcohol, gelatin, agar and the like.

Examples of the lubricant include stearic acid or metal salt thereof such as stearic acid, magnesium stearate, calcium stearate and the like, sucrose fatty acid ester, glycerol fatty acid ester, hydrogenated fats and oils, silicon dioxide, calcium phosphate and the like.

Examples of the sweetening agent include saccharin sodium, dipotassium glycyrrhizinate, aspartame, stevia, thaumatin, sucralose, glucose, fructose, saccharose and the like.

Examples of the colorant include Food Color Yellow No. 5, Food Color Red No. 2, Food Color Blue No. 2, carotenoid pigment, tomato pigment and the like.

Examples of the flavor include lemon flavor, lemon-lime flavor, grapefruit flavor, apple flavor, orange flavor and the like.

Examples of the antioxidant include tocopherol, cysteine hydrochloride and the like.

Examples of the glidant include calcium phosphate, calcium hydrogen phosphate, fine silicon dioxide and the like.

In addition to those mentioned above, saccharides other than the saccharides exemplified as the sweetening agent in the above such as xylose, galactose, trehalose, lactose, palatinose, maltitol, erythritol, sorbitol, xylitol, raffinose, inulo-oligosaccharide (chicory oligosaccharide), palatinose oligosaccharide and the like, vitamins such as niacin, vitamin A, vitamin B, vitamin D and the like, minerals such as sodium and the like, desiccant or anticaking agent such as fine silicon dioxide, calcium silicate, synthetic aluminum silicate, talc and the like, and the like may also be used.

When these substances are allowed to coexistence, they preferably coexist without being dissolved in a solvent such as an aqueous solvent (e.g., water, aqueous inorganic salt solution, buffer and the like), alcohol (e.g., methanol, ethanol, glycerol and the like), or a mixture thereof and the like.

The water content of the solid composition of the present invention obtained by achieving coexistence of these substances as mentioned above preferably does not exceed 5 wt %, more preferably does not exceed 3 wt %.

While the amount of glutathione and arginine in the solid composition of the present invention is not particularly limited, it is generally 10-90 wt %.

The method of improving preservation stability of the present invention can suppress decrease in the quality of glutathione in a solid composition containing glutathione and arginine, and can improve preservation stability.

The preservation stability of glutathione can be known as percentage of the content of glutathione after preservation to that of glutathione in the solid composition before preservation under predetermined conditions.

The solid composition of the present invention is formulated by using the composition as a starting material for formulation, and according to an ordinary method of formulating a general preparation, preferably a solid preparation, and can be used as the solid preparation of the present invention containing glutathione and arginine or a salt thereof and organic acid (e.g., powder, granule, tablet, capsule and the like).

For example, a powder can be produced by mixing powdery preparation starting materials in a mixing machine, or grinding the preparation starting materials in a grinding machine and the like, and mixing them in a mixing machine and the like.

Granules can be produced by granulating the preparation starting materials in a granulating machine.

A tablet can be produced by tableting preparation starting materials in a tableting machine.

After formulation, granule and tablet may be subjected to sugar coating using sugar, sugar alcohol and the like, film coating using a polymer, and the like.

A capsule can be produced by preparing a powder or granules and filling same in a hard capsule.

In addition to the above, solid preparations such as pill, troche, microcapsule and the like may be prepared according to a conventional method.

The solid preparation of the present invention containing glutathione and arginine can be utilized in the field of pharmaceutical product, food or feed. For administration to a human or non-human animal, 100 mg-20 g of glutathione and arginine or salts thereof is preferably administered per day.

Examples of the present invention are shown below.

Example 1

(1) To glutathione (0.5 g, manufactured by Kyowa Hakko Kogyo Co., Ltd., hereinafter the same) were added L-arginine (manufactured by Kyowa Hakko Kogyo Co., Ltd., hereinafter the same), L-glutamine (manufactured by Kyowa Hakko Kogyo Co., Ltd.), L-citrulline (manufactured by Kyowa Hakko Kogyo Co., Ltd.) and L-lysine (manufactured by Kyowa Hakko Kogyo Co., Ltd.) in the amounts indicated in Table 1, mixed, and the mixture was stirred to give powders 1-4.

The powders 1-4 were each placed in an aluminum pouch, and the pouch was tightly sealed and preserved at 60° C. for 2 weeks. After 2 weeks, a small amount was sampled from the aluminum pouch, and the content of glutathione was quantified by high performance liquid chromatography.

The conditions of high performance liquid chromatography are shown below.
column: Nucleosil 10-C18 4.6 mmΦ×250 mm (manufactured by GL Sciences, Inc.)
mobile phase: prepared by dissolving ammonium formate (2.84 g) in water, and adjusting the mixture to pH 4 with formic acid, adding water to the total amount of 1800 ml, adding methanol (200 ml) and stirring and deaerating the mixture.
detection wavelength: 280 nm
column temperature: 40° C.
mobile phase flow: 1.0 ml/min The residual rate of glutathione was calculated from the content of glutathione in each powder (powder 1-4) before preservation and that after preservation.

The results are shown in Table 1.

TABLE 1

| powder | glutathione content | components other than glutathione | content | glutathione residual rate (%) |
|---|---|---|---|---|
| 1 | 0.5 g | arginine | 10 g | 2% or below |
| 2 | | glutamine | 15 g | 94% |
| 3 | | citrulline | 5 g | 95% |
| 4 | | lysine | 5 g | 92% |

As shown in Table 1, in powder 1 containing L-arginine, the content of glutathione after the preservation decreased markedly.

(2) To each of glutathione (0.5 g) and L-arginine (10 g) was added citric acid in the amount indicated in Table 2 and mixed, and the mixture was stirred to give powders 5-7.

The powders 5-7 were each placed in an aluminum pouch, and the pouch was tightly sealed and preserved at 60° C. for 2 weeks. After 2 weeks, the residual rate of glutathione in each powder was calculated according to the method described in the above-mentioned (1).

The results are shown in Table 2.

TABLE 2

| | | | components other than glutathione | | |
|---|---|---|---|---|---|
| powder | glutathione content | component 1 | content | component 2 (organic acid) | content | glutathione residual rate (%) |
| 5 | 0.5 g | arginine | 10 g | citric acid | 4 g | 65% |
| 6 | | | | | 8 g | 56% |
| 7 | | | | | 12 g | 46% |

As shown in Table 2, addition of citric acid as an organic acid could suppress decrease in the quality of glutathione due to arginine.

(3) To each of glutathione (0.5 g) and L-arginine (5 g) was added organic acid indicated in Table 3 in the amounts indicated in Table 3 and mixed, and the mixture was stirred to give powders 8-11.

The powders 8-11 were each placed in an aluminum pouch, and the pouch was tightly sealed and preserved at 60° C. for 2 weeks. After 2 weeks, the residual rate of glutathione in each powder was calculated according to the method described in the above-mentioned (1).

The results are shown in Table 3.

TABLE 3

| | | | components other than glutathione | | |
|---|---|---|---|---|---|
| powder | glutathione content | component 1 | content | component 2 (organic acid) | content | glutathione residual rate (%) |
| 8 | 0.5 g | arginine | 5 g | citric acid | 2 g | 86% |
| 9 | | | | tartaric acid | | 86% |

TABLE 3-continued

| | | components other than glutathione | | | |
|---|---|---|---|---|---|
| powder | glutathione content | component 1 | content | component 2 (organic acid) | content | glutathione residual rate (%) |
| 10 | | | | ascorbic acid | | 85% |
| 11 | | | | malic acid | | 70% |

As shown in Table 3, addition of tartaric acid, ascorbic acid and malic acid as organic acids besides citric acid could suppress decrease in the quality of glutathione due to arginine.

INDUSTRIAL APPLICABILITY

The present invention can provide a method of improving preservation stability of glutathione in a solid composition containing glutathione and arginine, or a solid composition containing glutathione and arginine, which shows improved preservation stability of glutathione.

The invention claimed is:

1. A method of improving preservation stability of glutathione in a solid composition containing glutathione and arginine, which comprises achieving coexistence of glutathione and arginine, with an organic acid, in a solid composition containing 1 part by weight glutathione and 10-20 parts by weight of arginine relative to glutathione,
   wherein
   the organic acid is selected from the group consisting of citric acid, tartaric acid, and malic acid, and
   the organic acid is present in an amount of 0.4-0.8 parts by weight of organic acid relative to 1 part by weight of arginine.

2. The method according to claim 1, wherein the solid composition is a solid preparation.

3. The method according to claim 1, wherein the organic acid is citric acid.

4. A solid composition comprising glutathione, arginine, and citric acid or tartaric acid,
   wherein the composition comprises
   10-20 parts by weight of arginine relative to 1 part by weight of glutathione, and
   0.4-0.8 parts by weight citric acid or tartaric acid relative to 1 part by weight of arginine.

5. A solid preparation comprising glutathione, arginine, and citric acid or tartaric acid,
   wherein the preparation comprises
   10-20 parts by weight of arginine relative to 1 part by weight of glutathione, and
   0.4-0.8 parts by weight citric acid or tartaric acid relative to 1 part by weight of arginine.

6. The method according to claim 2, wherein the organic acid is citric acid.

7. The method according to claim 1, wherein the organic acid is present in an amount of 4-24 parts by weight of organic acid relative to 1 part by weight of glutathione.

8. The method according to claim 1, wherein the organic acid is tartaric acid.

9. The method according to claim 2, wherein the organic acid is tartaric acid.

* * * * *